United States Patent [19]
Visco et al.

[11] Patent Number: 5,711,029
[45] Date of Patent: Jan. 27, 1998

[54] PROTECTIVE APPARATUS FOR DISPERSING PRESSURE APPLIED AT A JOINT

[76] Inventors: Raymond D. Visco, P.O. Box 1755-303, Nederland, Colo. 80466; Stephen R. Koschmann, 345 Sunrise La., Boulder, Colo. 80302; Alden B. Hanson, 7046 Indian Peaks Trail, Boulder, Colo. 80301

[21] Appl. No.: 667,433

[22] Filed: Jun. 21, 1996

[51] Int. Cl.⁶ .............................. A41D 13/00; A61F 5/00
[52] U.S. Cl. .............................. 2/24; 2/455; 2/22; 602/26
[58] Field of Search .............................. 2/455, 24, 16, 2/22; 602/26, 20

[56] References Cited

U.S. PATENT DOCUMENTS

| | | | |
|---|---|---|---|
| Re. 34,573 | 4/1994 | Calvert | 2/267 |
| 588,907 | 8/1897 | Herbelin | |
| 1,786,268 | 12/1930 | Snavely | 2/24 |
| 2,195,817 | 4/1940 | Johnson | |
| 2,561,872 | 7/1951 | Krinick | |
| 2,568,083 | 9/1951 | Mitchell | |
| 2,657,385 | 11/1953 | Cushman et al. | 2/24 |
| 3,168,746 | 2/1965 | Smith | |
| 3,635,849 | 1/1972 | Hanson | |
| 4,255,202 | 3/1981 | Swan, Jr. | |
| 4,287,885 | 9/1981 | Applegate | |
| 4,370,978 | 2/1983 | Palumbo | |
| 4,378,009 | 3/1983 | Rowley et al. | 2/24 |
| 4,425,912 | 1/1984 | Harper | |
| 4,445,505 | 5/1984 | Labour et al. | |
| 4,484,360 | 11/1984 | Leighton et al. | 2/24 |
| 4,484,361 | 11/1984 | Leighton et al. | |
| 4,561,123 | 12/1985 | Hull | |
| 4,593,416 | 6/1986 | Figgie, III et al. | |
| 4,831,666 | 5/1989 | Denman | 2/24 |
| 4,876,745 | 10/1989 | Richards | |
| 4,920,577 | 5/1990 | Scharf | |
| 5,024,216 | 6/1991 | Shiono | |
| 5,031,240 | 7/1991 | Nierhaus | |
| 5,093,138 | 3/1992 | Drew et al. | |
| 5,093,931 | 3/1992 | La Berge et al. | 2/455 |
| 5,100,712 | 3/1992 | Drew et al. | |
| 5,131,174 | 7/1992 | Drew et al. | |
| 5,147,685 | 9/1992 | Hanson | |
| 5,159,717 | 11/1992 | Drew et al. | |
| 5,204,154 | 4/1993 | Drew et al. | |
| 5,525,292 | 6/1996 | Hargens | 2/24 |
| 5,537,689 | 7/1996 | Daryger | 2/24 |
| 5,551,084 | 9/1996 | Freese, III | 2/24 |

*Primary Examiner*—Bibhu Mohanty
*Attorney, Agent, or Firm*—Harold A. Burdick

[57] ABSTRACT

A joint protective apparatus is disclosed that is particularly well adapted to support and cushion the knee joint when kneeling. The apparatus includes a light weight, flexible support material wrap selectively positionable about the joint and having a retaining enclosure thereat positioned to be proximate the knee joint and upper shin area when properly positioned. A pad having plural compartments therein for containing a flowable material is receivable in, and substantially fills, the retaining enclosure. A relatively rigid yet deformable protective cap having a wedge shaped support platform configured to extend between the knee joint and the upper shin area is fastened to the wrap over the retaining enclosure.

18 Claims, 2 Drawing Sheets

5,711,029

PROTECTIVE APPARATUS FOR DISPERSING PRESSURE APPLIED AT A JOINT

FIELD OF THE INVENTION

This invention relates generally to skeletal joint protective devices such as supports or pads, and, more particularly, relates to knee or elbow support and/or cushioning devices utilized where constant pressure from an outside source is applied (such as is exhibited, for example, against the patella of the knee when kneeling).

BACKGROUND OF THE INVENTION

Tradesman in such fields as carpet laying, brick laying, roofing and flooring are often required to work in a kneeling position. Likewise, individuals who participate in such activities as gardening, photography, sporting events, archeology or the like also often kneel for long periods. In such cases, comfortable joint (knee or elbow) protection and support is necessary.

After a period of time, many such individuals (and particularly tradesmen) report knee problems. Common knee injuries associated with such activities include patellofemoral degeneration (pain and swelling around the knee cap), bursitis, patellar tendonitis, grating with flexation, and/or actual cartilage damage. One cause of such knee injuries has been found to be associated with prolonged compressive forces applied at the patellofemoral joint such as those exhibited when kneeling.

Numerous knee protective devices have been suggested and/or utilized over the years. Many such devices use foam or like padding material that, when kneeling, while positioning a cushion between the user and the kneeling surface, still allows pressure to be applied directly from the surface to the patella and/or patellofemoral joint (see, for example, U.S. Pat. Nos. 4,484,361, 4,593,416, and 4,561,123). Over time, despite the padding, this direct pressure on the patella may not prevent onset of many of the injuries discussed above.

Various knee braces or knee stabilizers have also been heretofore suggested and/or utilized which include a rigid outer cap over the knee (see, for example, U.S. Pat. Nos. 4,876,745 and 5,031,240). Such devices, however, are often bulky, overly inflexible (inhibiting free, non-binding user movement and/or demanding specific leg positioning of a user when kneeling) and uncomfortable to wear and use. Moreover, some such devices could tend to destabilize the user while kneeling due to a design which elevates the user's knee inordinately from the work surface. Further improvement in such devices could thus be utilized

SUMMARY OF THE INVENTION

This invention provides a skeletal joint protective apparatus that is particularly well adapted for use at the knee joint. The apparatus effectively disperses (redistributes) compressive forces applied at the patellofemoral joint (such as those exhibited when kneeling), is comfortable, light weight, and does not incumber user flexibility and stability when kneeling, standing or moving between such positions.

The protective apparatus includes a relatively rigid yet deformable support including a first portion adapted to conform to a user's knee area and a second portion extending away from said first portion and having increasingly greater material thickness in the direction of extension. A pad having flowable material with fluid-like characteristics contained therein is held adjacent to the support to be between the user's knee and the support when the apparatus is in use.

The second portion of the support extends from the first portion to a position adapted to bear the user's upper shin, the second portion having a wedge-like configuration between a first surface positionable adjacent to the user and a second surface adapted for contacting the structure. The second surface of the second portion of the support is relatively flat, begins at the first portion of the support and extends to a terminus spaced from the first portion, and is broader adjacent to the terminus than adjacent to the first portion.

A flexible wrap including means adapted for securement of the wrap around a selected joint of a user is provided, the wrap having a retaining member positioned on the wrap so that, when the wrap is secured around the joint, the retaining member is proximate to the joint. The pad is securable at the retaining member of the wrap.

The pad includes plural compartments defining the containment area, at least one of the compartments positioned to cushion and support the joint and at least another of the compartments positioned to cushion and support an adjacent skeletal member such as the upper shin.

It is therefore and object of the invention to provide a knee joint protective apparatus that effectively disperses or redistributes compressive forces applied at the patellofemoral joint.

It is another object of this invention to provide a knee support and cushioning apparatus that is comfortable, light weight, and does not incumber user movement, flexibility and stability when kneeling.

It is still another object of this invention to provide a protective apparatus positionable between a user's knee area and a structure into which the knee area may come into contact, the apparatus having a relatively rigid yet deformable support including a first portion adapted to conform to a user's knee area and a second portion extending away from the first portion and having increasingly greater material thickness in the direction of extension, a pad having flowable material with fluid-like characteristics contained therein being held adjacent to the support to be between the user's knee and the support when the apparatus is in use.

It is still another object of this invention to provide a flexible joint support and cushioning apparatus that includes a flexible wrap having means adapted for securement of the wrap around a selected joint of a user, the wrap having a retaining member positioned on the wrap so that, when the wrap is secured around the joint, the retaining member is proximate to the joint, and an enclosure defining a containment area and securable at the retaining member of the wrap, flowable material being held in the containment area of the enclosure, with the retaining member of the wrap, the enclosure and the material selected and configured to provide cushioning and support at both the user's joint and an adjacent skeletal member.

It is yet another object of this invention to provide a knee support and cushioning apparatus for dispersing patellar pressure normally exhibited when kneeling by redistributing support so that at least some weight is borne at a user's upper shin, the apparatus comprising a flexible wrap including means adapted for securement of the wrap around a user's knee, the wrap having a main body shaped and positioned on the wrap so that, when the wrap is secured around the knee, the main body is proximate to the user's knee and upper shin, and a relatively rigid yet deformable support connectable to the flexible wrap over the main body thereof, the support including a first portion adapted to conform to the use's knee and a second portion extending away from the first portion and adapted to bear the user's upper shin, the second portion having increasingly greater material thickness in the direction of extension.

With these and other objects in view, which will become apparent to one skilled in the art as the description proceeds, this invention resides in the novel construction, combination and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
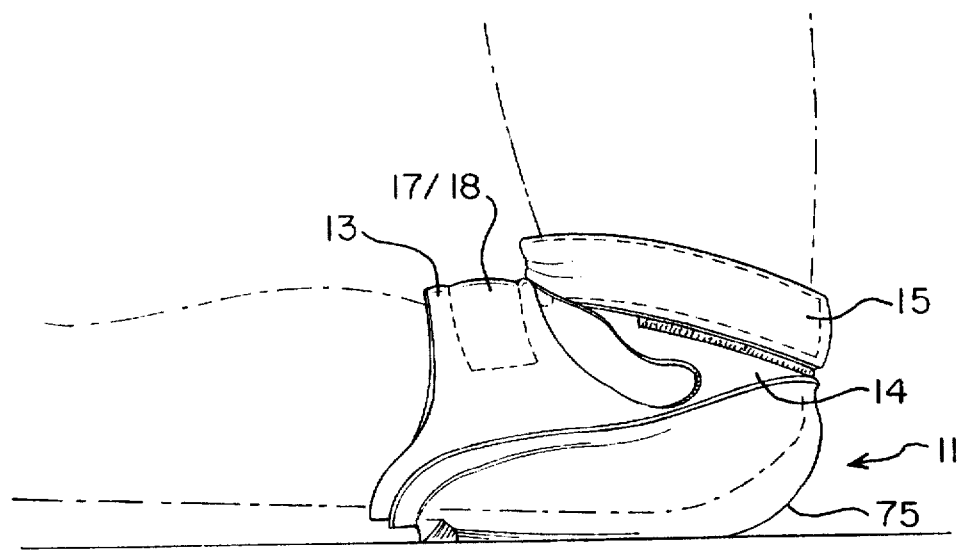
FIG. 1 is a side elevation view of the apparatus of this invention applied at the knee of a user's leg.
Figure 3:
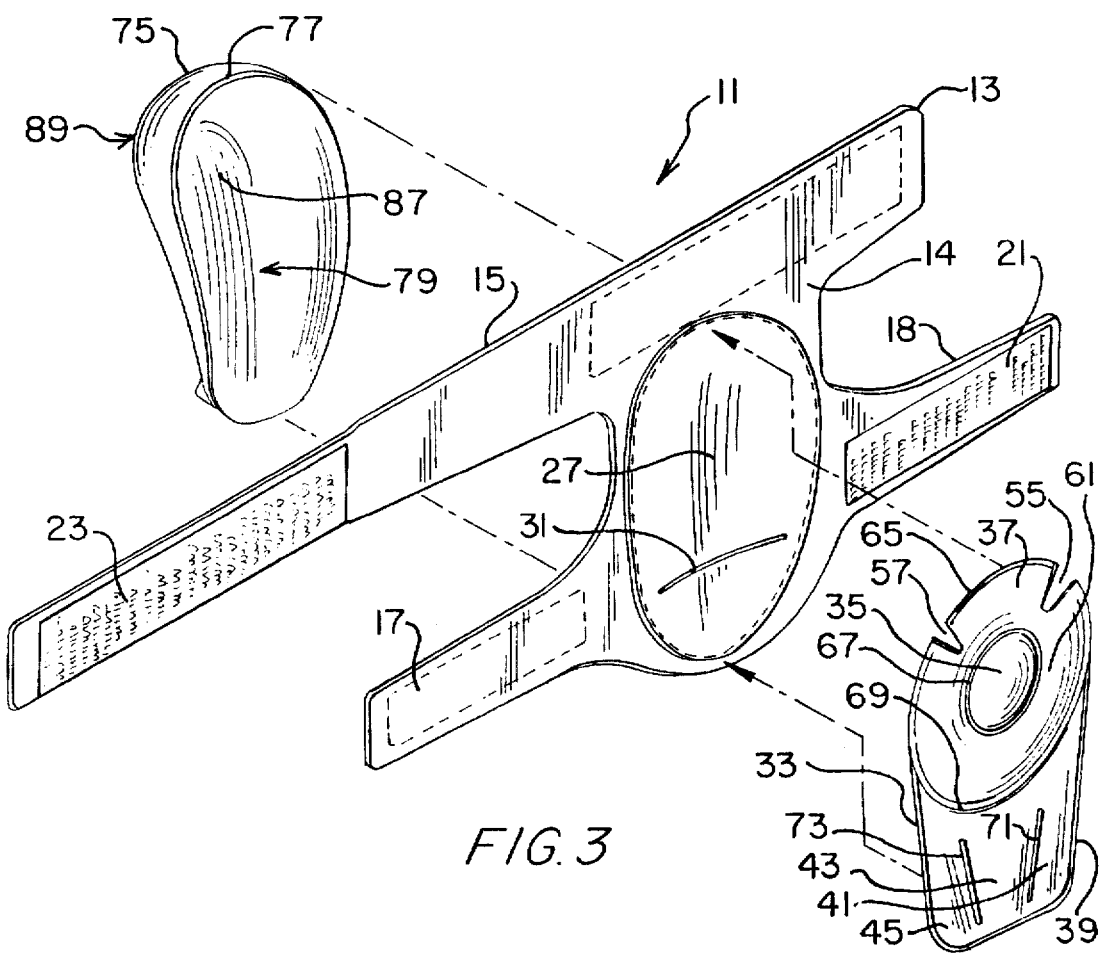
FIG. 3 is reverse exploded view of the apparatus of FIG. 1.
Figure 2:
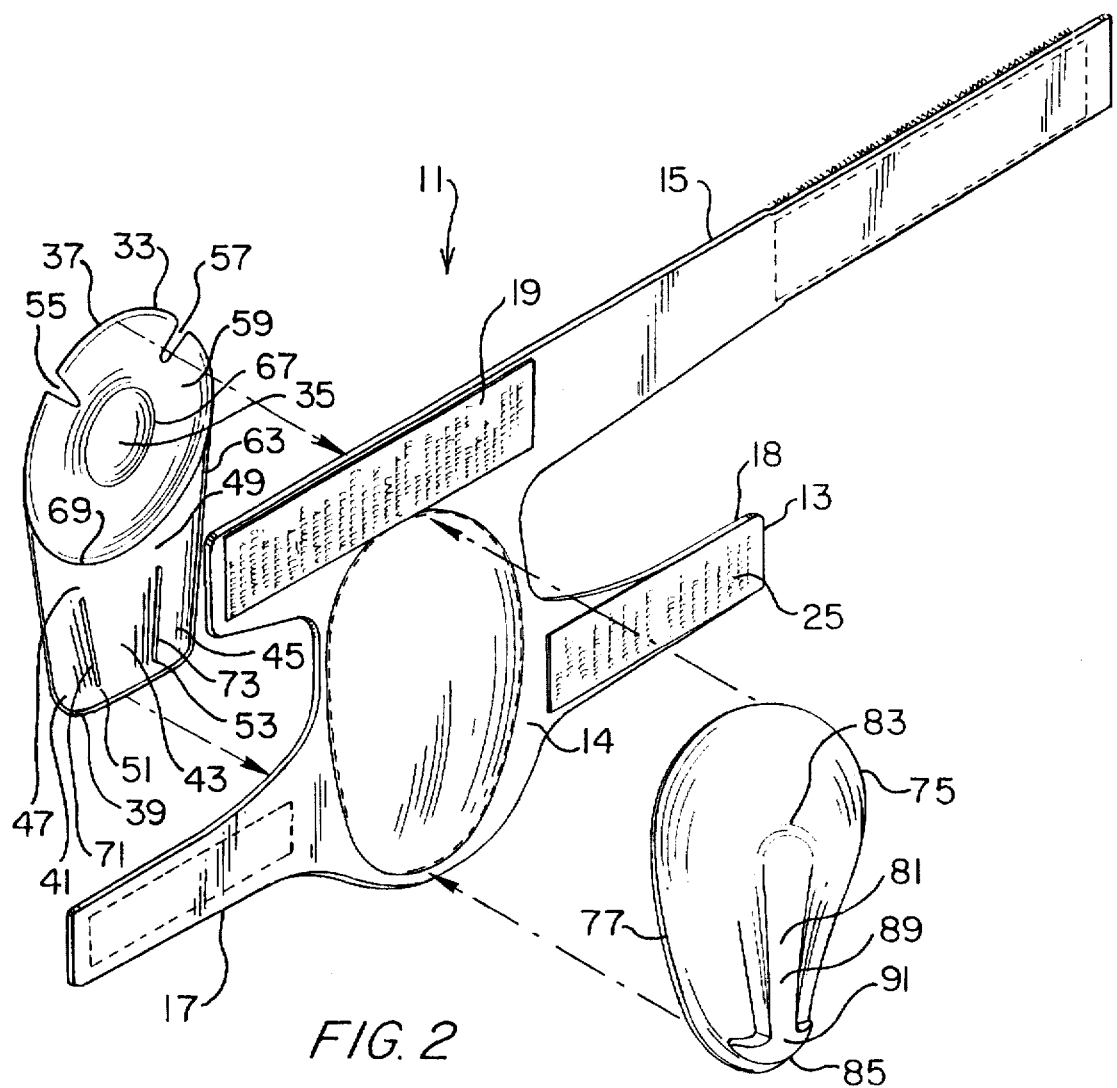
FIG. 2 is an exploded view of the apparatus of FIG. 1.
Figure 4:
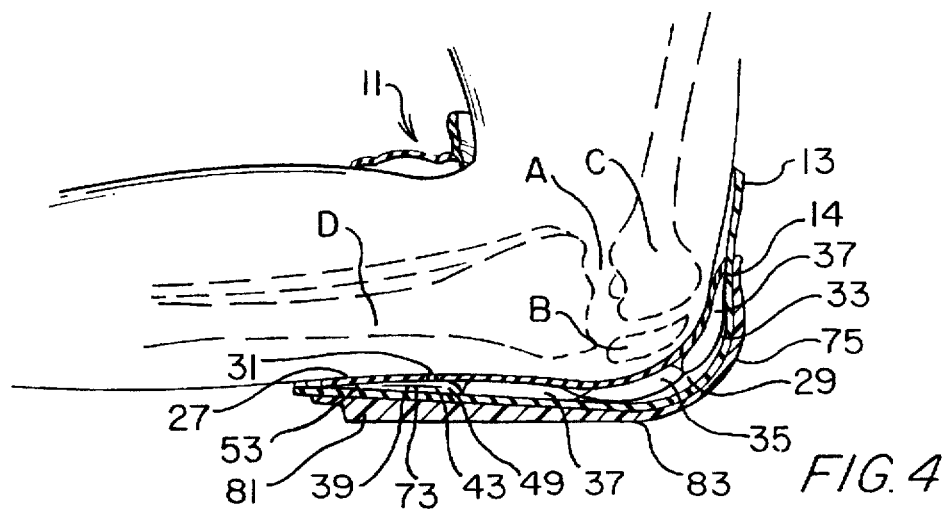
FIG. 4 is a partial sectional view (illustrating all but the attachment straps) of the apparatus of FIG. 1.

The apparatus of this invention, utilizable on any skeletal joint, but in particular joints such as the knee or elbow, is illustrated in use at the knee of a user in a kneeling position in FIGS. 1 and 4. Apparatus 11 shown therein (and in FIGS. 2 and 3) includes light weight support material wrap 13 for securement around the user's knee area (covering, as shown in FIG. 4, knee joint A, patella B, lower femur C and upper tibia and shin D).

Wrap 13 is preferably constructed of a single piece of thin, flexible and breathable stretch material such as neoprene or the like. Wrap 13 is asymmetrically configured and includes protective main body 14 and upper and lower straps 15 and 17/18, respectively, to provide means for both securing and adjusting the position and fit of wrap 13 on a the user's knee. Securement and adjustment may be provided, for example, utilizing hook and loop fabric connectors (such a VELCRO brand type material), with hook connectors 19 and 21 and matable loop connectors 23 and 25 being attached (sewn or glued, for example) to their respective straps 15 add 17/18. Hook and loop connectors 19 and 23 at upper strap 15 are positioned so that the ends of the strap with the connectors thereat are presented at the front of the lower thigh when applied, thus allowing apparatus 11 to be easily put on, taken off, and/or repositioned. The ends of lower straps 17/18 are positioned to wrap around the upper calf and be attached at the back of the leg. With both straps attached, main body 14 is positioned to completely cover the patella B (extending beyond the sides of, as well as above and below the patella), and extend to a position covering the upper shin D of the user's leg (see FIG. 4).

Main body 14 has flexible material member 27 connected at the interior thereof (for example, by sewing) thus defining retaining enclosure 29 (FIG. 4) between main body 14 and member 27. Material member 27 is made from material the same or similar to, that forming wrap 13, and has opening (or slot) 31 formed therein for access to the interior of enclosure 29. Material member 27 is of a size sufficient so that, when positioned, it will cover the same areas of the leg as main body 14 (see FIG. 4).

Pad 33 having a flowable material enclosed therein is receivable in and removable from retaining enclosure 29 through opening 31, thereby accommodating pad replacement (for example, various pads having different flow characteristics and weights, as discussed below, might be chosen for different applications or for user's of different weights). Pad 33 includes discreet material filled compartments 35, 37 and 39, each isolated against flow of material contained therein from one compartment to another. As shown in FIG. 4, compartment 35 is shaped to cover and cushion the patella B of a user when kneeling, while compartment 37 is shaped to provide perimeter support of the patella B. Compartment 39 is shaped to provide support, both directly (between upper shin D and a kneeling surface) and laterally, between the patella B and the upper shin D to thereby redistribute support and weight, and thus patellar pressure, to the upper shin D when the user is kneeling.

Pad compartments 35, 37 and 39 are filled with varying amounts of flowable material selected to alleviate the point pressure on the patella and maximize redistribution of the weight of the persons body around the perimeter of patella B and to the upper shin D, and to fill and support the wedge-shaped area beneath the upper shin area (as shown in FIG. 4).

Compartment 39 is further formed with interconnected elongated flow chambers 41, 43 and 45 arranged in side by side fashion (i.e., with an end of each of the chambers adjacent to compartment 37) to direct and prevent improper (overly rapid, for example) movement of the flowable material, and to accommodate continued support as the user shifts body weight. Sufficient flowable material is contained in compartment 39 to assure that no one of the chambers "bottoms out" (is completely or substantially emptied of material) when pressure is applied thereto while yet accommodating material flow into an adjacent one or ones of the chambers (through passages at 47, 49, 51 and 53 of FIGS. 2 and 4). In this fashion, pad and user stability while the user is kneeling is maintained.

Compartment 35 preferably contains a lesser amount of the flowable material than compartments 37 or 39 to thus create a depression in which the patella B can freely float (i.e., remain free of pressure when the user kneels). Wedge cutouts 55 and 57 allow pad 33 to conform to the hemicylindrical shape of the knee and upper shin area of the leg.

Pad 33 is formed using sheets 59 and 61 (FIGS. 2 and 3) each having the desired shape of the pad and which are joined at their outer perimeters 63 and 65, respectively, to form a material containment area between the sheets. Upper and lower sheets 59 and 61 of pad 33 may be made of various materials including any flexible light weight, preferably pliable material having a certain degree of elasticity and resistance to puncturing. Materials having a thickness of between about 0.1 and 0.8 millimeters, depending on the material are typical. Polyurethane, polyvinyl, acetal, acrylic, cellulosic, chlorinated polyether, flourocarbon (TFE, CTFE, or FEP), nylon (polyamide), polycarbonate, polyetheylene, polystyrene, polyester, and polysulfone materials could all be utilized (preferably 0.2 millimeter polyurethane). If desired, convexivity may be introduced into sheets 59 and/or 61, for example by vacuum forming.

After cutting sheets 59 and 61 into the desired shape, upper and lower surface sheets are affixed to each other, for example, by heat sealing or other methods known to those skilled in the art. Compartments 35, 37 and 39 and chambers 41, 43 and 45 are likewise formed by affixing the sheets to each other (along seems 67 and 69 for the compartments, and along flow barrier seems 71 and 73 having unobstructed passages 47, 49, 51 add 53 defined thereby in the case of chambers 41, 43 and 45.) by heat sealing or the like. The seals between the sheets are a substantially flat surface. A small opening is left (in each compartment seal unless the pad is prefilled) for insertion of a filling apparatus into the thus formed compartment. The filling apparatus is inserted into the opening and a predetermined volume of the flowable material is placed into the compartment or compartments of the pad. The filling apparatus is then removed and the opening is sealed. It is to be realized, that the cutting of the material into the final shape of the pad may occur at any time during the process.

While it is typically unnecessary to remove air from the compartments prior to sealing (because air will also act as a shock absorbing medium), air removal can be performed if desired (i.e., where a pad having no "bounce" is desired) prior to sealing of the opening so that only flowable material will occupy the containment area of the of the compartments.

The size of pad 33 should be slightly larger (approximately 10%) than the surface area of patella B and upper shin area D being supported. The shape of the upper and lower surface sheets and/or the compartments when formed by sealing determines the range of lateral movement of the pad which occurs pursuant to user applied forces, and thus a variety of compartment shapes may be utilized in this invention.

The volume of fluid contained in each compartment 35, 37 and 39 of pad 33 of this invention would typically be about 25% to 95% of the maximum volume capacity of the enclosure (achievable without significant deformation of the enclosure material). As the fill volume approaches the upper part of this range, stability of the pad decreases. In other words, the force required to laterally move the pad decreases. However, increased viscosity of the material tends to increase stability of the pad because of the greater applied forces required to cause pad movement. The variation of fill volume to fill material viscosity is thus utilizable to achieve a variety of pad characteristics. Other variables utilized to vary pad characteristics (desired flow characteristics, pad movement, pressure responsiveness and pad rebound or memory) include higher durometer and thicker upper and lower surface sheet materials, and pad size, volume and seam placement and length.

The flowable material utilized to occupy the containment area of the compartments of the pad may be any flowable material which reacts to an applied force by migrating to other regions of the pad compartment to more effectively distribute forces over a larger area of the pad. Thus the material must exhibit fluid-like characteristics. Materials such as wax, glycerin, water, salt water, grease, fats, oils, propylene glycol, syrup and even air or some particle materials either alone or in mixture with a fluid material may thus be used. Other appropriate flowable materials are HB Fuller 1454 Hot Melt (a flowable microcrystalline wax) and glycerine and the various materials produced by Alden Laboratories, Inc. under the trademark FLOLITE (either of which are preferred for their nontoxicity). The preferred FLOLITE materials are compositions including wax, oil and glass micro-spheres. For more detailed disclosure of some such materials that may be appropriate for use with this invention see U.S. Pat. Nos. 5,204,154, 5,100,712, 5,093,138, 4,255,202 and 3,635,849.

Preferred materials for use with this invention, such as the above-mentioned FLOLITE materials, are flowable while not having total memory. In other words once deformed, the pad will not always return to its original shape. However, some materials appropriate for use in this invention do exhibit a degree of gel strength, the gel structure being broken merely by applying a small but sufficient force to the pad, and these materials are preferred for the pads used in this invention in many applications.

Many of the above mentioned FLOLITE materials, and the flowable material preferably utilized in this invention, behave in an non-Newtonian manner, because their viscosities change when the shear rate changes. In other words, the ratio of shear rate (flow) to shear stress (force) is not constant. These materials are typically either pseudoplastic or thixotropic. A pseudoplastic material is one which appears to have a yield stress beyond which flow commences and increases sharply with an increase in stress. In practice, the materials exhibit flow at all shear stresses, although the ratio of flow to force increases negligibly until the force exceeds the apparent yield stress. The flow rate of a thixotropic material increases with increasing duration of agitation as well as with increased shear stress. In other words, the flow rate is time dependent. When agitation is stopped, internal shear stress can exhibit hysteresis. Upon re-agitation, less force is generally required to create a given flow than is required for the first agitation. The fact that the materials preferably used in this invention flow more readily when higher shear stress is applied is advantageous.

The flowable materials used in pad 33 have a viscosity in a range of between about 50 and 250,000 centipoise (preferably between about 10,000 and 250,000 centipoise), and are selected to provide good pressure distribution throughout the entire area of the body in contact with the pad. For applications where no or reduced cold flow (i.e. the tendency to flow to its own weight) is desired, for example to achieve a pad having memory, the viscosity of the material should be in the 150,000 to 250,000 centipoise range. For applications preferably allowing a greater degree of pad movement and responsiveness to movement, a less viscous material (between about 50 and 100,000 centipoise, and preferably between about 5,000 and 10,000 centipoise) is required.

Protective support cap 75 is fastened to the outside of wrap 13 (opposite the side of material member 27) by stitching (utilizing any strong material, such a nylon monofilament, along outer ridge 77) and/or gluing (fastening means of a less permanent nature, such as hook and loop materials, for allowing selective removal of cap 75 could also be utilized). Cap 75 is of a size and is positioned to completely cover and contain the area of pad 33, and is of generally hemi-cylindrical shape, configured at the inner cavity 79 thereof to comfortably conform to the knee and shin area, thus covering the area from above the knee to the upper shin area of the lower leg. While not shown herein, inner cavity 79 may be lined to provide greater durability and wrap fabric wear.

Cap 75 is made of any durable relatively rigid yet deformable material, for example bench poured or molded polyurethane having a durometer of between 60 and 90 (preferably about 80) with a material thickness in most regions of about one millimeter. Flat, stable support platform 81 extends from upper, patella covering, portion 83 to a terminus 85 spaced from portion 83 a distance sufficient to support the upper shin D. Platform 81 has an ever increasing material thickness between inner surface 87 and outer flat surface 89 thereof in the direction of extension, reaching a thickness of no greater than about two inches (preferably about 1 ⅝") at terminus 85 and thus defining a wedge. In conjunction with pad 33, the wedge shaped construction of platform 81 effectively redistributes the weight of a kneeling user of apparatus 11 along the upper shin area D from patella B.

Flat platform 81 includes a broadened (tee-shaped) area 91 at terminus 85 to assure stability of a user when kneeling (i.e., allowing a full range of motion when working in a kneeling position without tipping from its center position). Portion 83 of cap 81 includes a gentle radius to allow for rolling forward or sideward, thus maintaining user flexibility when reaching for an object that is in front of or to the side of the kneeling user.

Of course, it is to be realized that the apparatus illustrated herein would often be used in pairs (one for each knee), though use of the apparatus for one knee (or other joint) is also contemplated. While a specific preferred mode of the invention has been described herein, it should be realized that a number of modifications or application specific embodiments fall within the scope of this invention. For example, wrap 13 and pad 33 could be utilized with or without wrap 13 utilized with or without pad 33. Furthermore, cap 81 and pad 33 could be incorporated as a single unit and used with wrap 13 (or other securing device) or independently of any securing device (i.e., as free standing shoes, for example).

What is claimed is:

1. A protective apparatus positionable between a user's knee area and a structure into which the knee area may come into contact, said apparatus comprising:

a relatively rigid yet deformable support including a first portion adapted to conform to a user's knee area and a second portion extending away from said first portion to a position adapted to bear the user's upper shin when said apparatus is in use, said second portion having a wedge-like configuration of increasingly greater material thickness in the direction of extension and residing between a first surface positionable adjacent to the user and a relatively flat second surface adapted for contacting the structure, said second surface of said second portion of said support beginning at said first portion of said support and extending in the direction of extension to a terminus spaced from said first portion, said second surface being broader adjacent to said terminus than adjacent to said first portion; and a pad having flowable material with fluid-like characteristics contained therein, said pad held adjacent to said support to be between the user's knee and said support when said apparatus is in use.

2. The apparatus of claim 1 further comprising flexible means adapted for holding said support and said pad adjacent to the user's knee area.

3. The apparatus of claim 1 wherein said second portion of said support has a material thickness no greater than about two inches between said first and second surfaces thereof.

4. The apparatus of claim 1 wherein said pad includes a plurality of discrete compartments each containing a volume of said flowable material, at least one of said compartments being adapted to fit adjacent to said second portion of said support.

5. A flexible joint support and cushioning apparatus utilized to protect a user's joint when in contact with a working surface, said apparatus comprising:

a flexing wrap including means adapted for securement of said wrap around a selected joint of a user, said wrap having a retaining member positioned on said wrap so that, when said wrap is secured around the joint, said retaining member is proximate to the joint;

a relatively rigid yet deformable support affixed at said flexible wrap at a position corresponding with said retaining member of said wrap, said support including a first portion adapted to conform to the joint and a second portion extending away from said first portion, said second portion residing between a first surface positionable adjacent to the user when said wrap is secured around the joint and a relatively flat second surface adapted for contacting the working surface, said second surface of said second portion of said support beginning at said first portion of said support and extending in the direction of extension to a terminus spaced from said first portion, said second surface being broader adjacent to said terminus than adjacent to said first portion;

an enclosure defining a containment area and securable at said retaining member of said wrap;

flowable material in said containment area of said enclosure; said said retaining member of said wrap, said enclosure and said material selected and configured to provide cushioning and support at both the user's joint and an adjacent skeletal member.

6. The apparatus of claim 5 wherein said flowable material is a pressure compensating composition exhibiting a non-constant shear rate to shear stress ratio.

7. The apparatus of claim 5 wherein said flowable material has fluid like characteristics and is resistant to cold flow.

8. The apparatus of claim 5 wherein said enclosure includes plural compartments defining said containment area, at least one of said compartments positioned to cushion and support the joint and at least another of said compartments positioned to cushion and support the adjacent skeletal member.

9. The apparatus of claim 5 wherein said joint is the knee and wherein said adjacent skeletal member is the upper shin, said containment area of said enclosure including a first compartment configured to cushion the user's knee, a second compartment surrounding said first compartment, and a third compartment extending from said second compartment and configured to cushion and support the user's upper shin, each of said compartments containing said flowable material and sealed from one another against material flow therebetween.

10. The apparatus of claim 9 wherein said third compartment includes plural chambers interconnected to provide selected material flow characteristics therebetween.

11. The apparatus of claim 10 wherein said plural chambers of said third compartment include at least three elongated chambers arranged side by side and each having a first end adjacent to said second compartment.

12. The apparatus of claim 10 wherein said third compartment contains a volume of flowable material selected so that no one of said plural chambers is emptied of said flowable material when pressure is applied thereto while yet accommodating material flow into another of said plural chambers.

13. The apparatus of claim 5 wherein said retaining member of said flexible wrap includes an opening for insertion and removal of said enclosure.

14. A knee support and cushioning apparatus for dispersing patellar pressure normally exhibited when kneeling by redistributing support so that at least some weight is borne at a user's upper shin, said apparatus comprising:

a flexible wrap including means adapted for securement of said wrap around a user's knee, said wrap having a main body shaped and positioned on said wrap so that, when said wrap is secured around the knee, said main body is proximate to the user's knee and upper shin; and a relatively rigid yet deformable support fastened to said flexible wrap over said main body thereof, said support including a first portion adapted to conform to the user's knee and a second portion extending away from said first portion to a terminus and adapted to bear the user's upper shin, said second portion having increasingly greater material thickness in the direction of extension with greatest material thickness at said terminus and having a tee-shaped configuration at said terminus to provide greater user stability when the user is in the kneeling position.

15. The apparatus of claim 14 wherein said wrap includes a retaining enclosure at said main body positioned to be proximate the user's knee and upper shin when said wrap is secured, said apparatus further comprising a pad shaped to be received by and substantially fill said retaining enclosure of said flexible wrap.

16. The apparatus of claim 15 wherein said pad has plural compartments defining a containment area for containing a flowable material, with at least one of said compartments positioned to cushion and support the knee and at least another of said compartments positioned to cushion and support the upper shin.

17. The apparatus of claim 16 wherein a first of said plural compartments of said pad is configured to provide a patellar cushion for the user's knee, wherein a second of said plural compartments surrounds said first compartment, and wherein a third of said plural compartments extends from said second compartment and is configured to cushion and support the user's upper shin, each of said compartments containing said flowable material and sealed from one another against material flow therebetween.

18. The apparatus of claim 14 wherein said second portion of said support has a wedge-like configuration between a first surface adjacent to said retaining enclosure of said flexible wrap and a second surface adapted for contact with structure upon which the user kneels.

* * * * *